United States Patent
Cosman

(10) Patent No.: US 6,459,769 B1
(45) Date of Patent: Oct. 1, 2002

(54) MOVABLE MINIATURE MULTI-LEAF COLLIMATOR

(75) Inventor: Eric R. Cosman, Belmonth, MA (US)

(73) Assignee: Sherwood Services AG, Schaffhausen (CH)

(*) Notice: Subject to any disclaimer, the term of this patent is extended or adjusted under 35 U.S.C. 154(b) by 0 days.

(21) Appl. No.: 09/560,734

(22) Filed: Apr. 28, 2000

Related U.S. Application Data

(60) Provisional application No. 60/132,247, filed on May 3, 1999.

(51) Int. Cl.$^7$ .................................................. G21K 1/04
(52) U.S. Cl. ...................... 378/147; 378/151; 378/152; 378/153; 378/65; 250/505.1
(58) Field of Search ...................... 250/505.1; 378/147, 378/151, 152, 153, 65

(56) References Cited

U.S. PATENT DOCUMENTS

| | | | |
|---|---|---|---|
| 4,739,173 A | 4/1988 | Blosser et al. ............ 250/505.1 |
| 4,754,147 A | 6/1988 | Maughan et al. ......... 250/505.1 |
| 4,868,843 A | 9/1989 | Nunan ......................... 378/152 |
| 4,868,844 A | 9/1989 | Nunan ......................... 378/152 |
| 4,897,861 A | 1/1990 | Schafter et al. ............. 378/150 |
| 4,987,309 A | 1/1991 | Klasen et al. ............ 250/492.1 |
| 5,080,100 A | 1/1992 | Trotel ....................... 128/653.1 |
| 5,160,847 A | 11/1992 | Leavitt et al. ............ 250/505.1 |
| 5,165,106 A | 11/1992 | Barthelmes et al. ..... 250/505.1 |
| 5,166,531 A | 11/1992 | Huntzinger ............... 250/505.1 |
| 5,168,531 A | * 12/1992 | Huntzinger ............... 250/505.1 |
| 5,216,255 A | 6/1993 | Weidlich .................. 250/492.3 |
| 5,317,616 A | 5/1994 | Swerdloff et al. ............. 378/65 |
| 5,332,908 A | 7/1994 | Weidlich ................. 250/492.1 |
| 5,351,280 A | 9/1994 | Swerdloff et al. ............. 378/65 |
| 5,438,991 A | 8/1995 | Yu et al. .................. 128/653.1 |
| 5,553,112 A | 9/1996 | Hardy et al. ................. 378/206 |
| 5,555,283 A | 9/1996 | Shiu et al. .................. 378/151 |
| 5,563,925 A | 10/1996 | Hernandez .................. 378/150 |
| 5,591,983 A | * 1/1997 | Yao .......................... 250/505.1 |
| 5,621,779 A | 4/1997 | Hughes et al. ................ 778/65 |
| 5,668,847 A | 9/1997 | Hernandez .................... 378/65 |
| 5,748,703 A | * 5/1998 | Cosman ...................... 378/152 |
| 5,778,043 A | 7/1998 | Cosman ........................ 378/65 |
| 5,818,902 A | 10/1998 | Yu ............................... 378/65 |
| 5,847,403 A | 12/1998 | Hughes et al. ........... 250/505.1 |
| 5,889,843 A | 3/1999 | Vilsmeier et al. ........... 378/147 |
| 6,005,919 A | 12/1999 | Kooy et al. ................. 378/147 |
| 6,041,101 A | 3/2000 | Kooy et al. ................. 378/147 |

* cited by examiner

Primary Examiner—Bruce Anderson
Assistant Examiner—Nikita Wells

(57) ABSTRACT

A method and system for shaping a beam from a radiation delivery device includes a moving miniature multi-leaf collimator which can be moved into the field of radiation from the radiation device to shape the beam or moved out of the radiation field of the radiation device so that a second collimator can shape the beam. The movable miniature multi-leaf collimator comprises opposing banks of movable leaves to form a conformal shape when the collimator is within the radiation field. A translation or rotation mechanism can move the left and right leaf banks at the collimator away from and displaced significantly from the radiation beam of the radiation delivery device so that they will not intercept the radiation field. A second collimator device is then used to produce another independent beam shaping within the radiation field of the radiation device. The miniature multi-leaf collimator is adapted to be so displaced into and away from the radiation field without being physically removed from the radiation device.

9 Claims, 4 Drawing Sheets

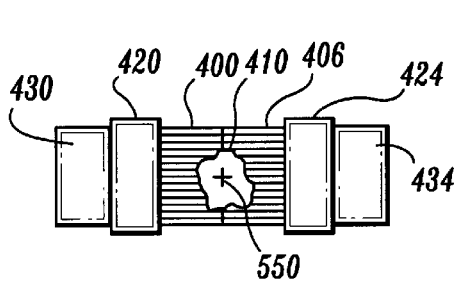
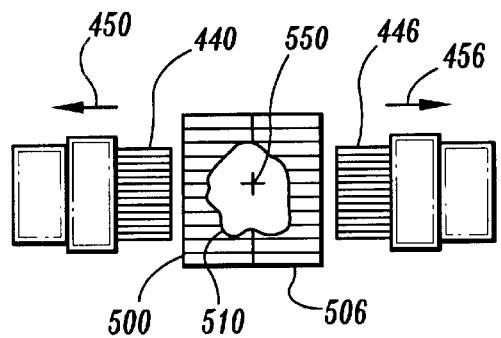
FIG. 6A    FIG. 6B
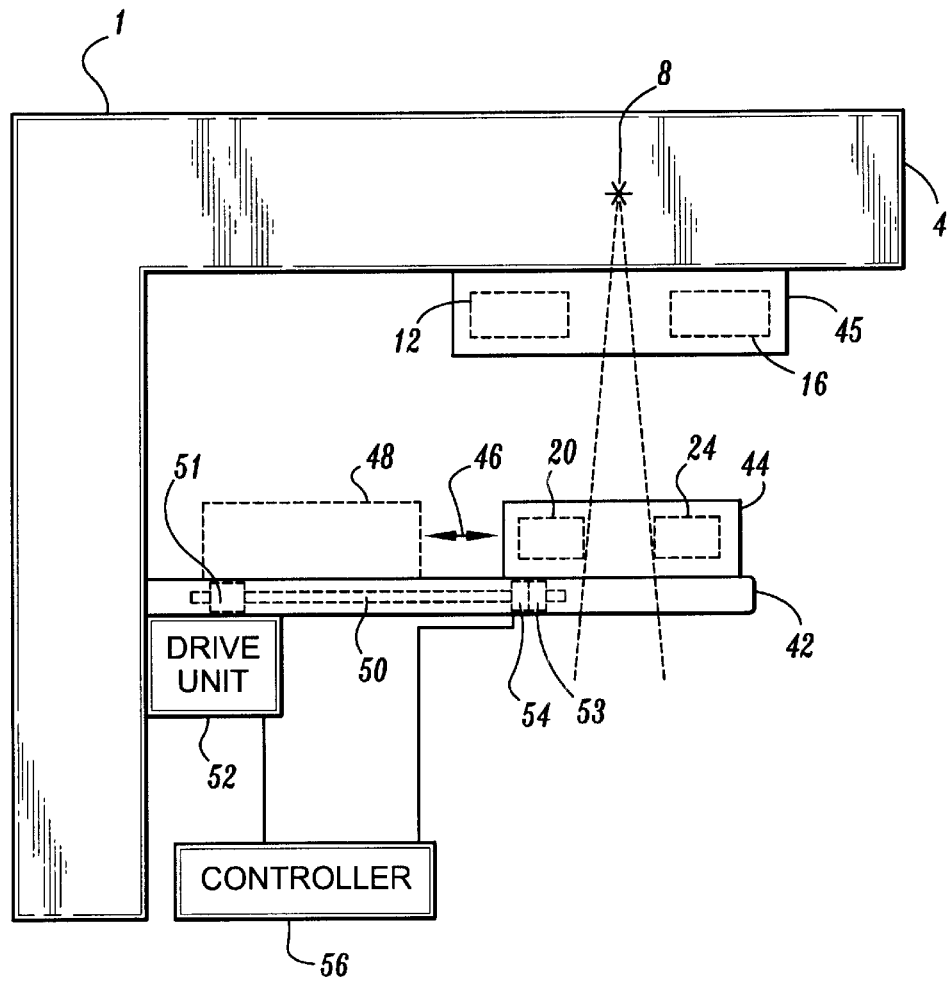
FIG. 7

MOVABLE MINIATURE MULTI-LEAF COLLIMATOR

This application claims the benefit of provisional application Ser. No. 60/132,247, filed May 3, 1999.

FIELD OF THE INVENTION

This invention relates generally to technological advances in the medical field and systems and procedures for prolonging and improving human life. More particularly, this invention relates to a method and system for moving a miniature multi-leaf collimator which remains attached to a linear accelerator or other source of radiation to provide alternative modes of radiation beam shaping. In one mode the beam shaping is determined by the miniature multi-leaf collimator when the collimator is positioned within the beam projection that emanates from the radiation source. In a second mode the beam is defined by another collimator system when the miniature multi-leaf collimator is positioned out of the beam projection. Thus, two alternate fields can be achieved for a fixed patient position and radiation beam position by movement of the miniature multi-leaf collimator without removing the collimator from the radiation device.

BACKGROUND TO THE INVENTION

Computer-controlled, motorized, mechanical multi-leaf collimators have been applied to produce conformal shaping of radiation beams. By way of example, the multi-leaf collimator for linear accelerators (LINAC's) are available from Varian, Inc. (Palo Alto, Calif.) and Siemens Oncology Care Systems, Inc. (Concord, Calif.). Such multi-leaf collimators typically have tungsten leaves with widths of approximately one centimeter. The multiple tungsten leaves provide conformal beam shaping of X-ray beams from the LINAC. Conformnal radiation doses can be achieved using multi-leaf collimators to conform more closely to a target volume such as a tumor in the patient's body.

Miniature multi-leaf collimators (MMLCs) are also used for finer confirmation of radiation beams. By way of example, the miniature multi-leaf collimator from Radionics, Inc. (Burlington, Mass.) and the M3 micro multi-leaf collimator from BrainLAB GmbH (Munich, Germany) provides finer beam confirmation than standard multi-leaf collimators, such as those referenced above from the Varian and Siemens companies. The leaf widths for a miniature multi-leaf collimator are typically thinner than those for a multi-leaf collimator. For example, the MMLC of Radionics, Inc. has tungsten leaves of four millimeter thickness. The miniature multi-leaf collimators are mounted and de-mounted from the linear accelerator during application. When finer confirmation for stereotactic radiosurgery or conformal stereotactic radiotherapy is desired, the miniature multi-leaf collimator can be mounted and secured to the radiation head of a LINAC. When the treatment is completed, the miniature multi-leaf collimator can be removed from the linear accelerator. In some cases, a micro multi-leaf collimator may be permanently mounted in a fixed position on a LINAC. See, for example, the NOVALIS LINAC system from BrainLAB, Inc., which is a combination of a Varian LINAC and a BrainLAB micro multi-leaf collimator. The NOVALIS accelerator is used for beam shaping only for the situation where beam shapes are provided by the micro multi-leaf collimator used in a conformal beam mode.

The procedure of mounting and de-mounting a miniature multi-leaf collimator from a LINAC requires time and additional quality assurance checks. During the busy daily use of a LINAC for radiation therapy, the steps of mounting and de-mounting a miniature multi-leaf collimator can be inefficient and extend the time of treatment using the miniature multi-leaf collimator. Furthermore, the mounting and de-mounting of a miniature multi-leaf collimator presents a safety hazard, since there is the possibility that improper mounting could lead to the miniature multi-leaf collimator moving or even falling. This could be a safety hazard for the patient who is being treated on the LINAC.

There are other disadvantages of a mountable and de-mountable miniature multi-leaf collimator or a miniature multi-leaf collimator that is mounted permanently and in a fixed position on the LINAC. For example, it may be difficult to use such a collimator to deliver treatments which use combined fields such as miniature multi-leaf conformed fields and larger fields which are shaped by a larger multi-leaf collimator or other radiation shaping devices such as cut blocks, wedges, radiation jaws, and similar devices. In addition, in some clinical applications it is desirable in the treatment of a specific patient at a particular radiation beam angle to use a narrow conformal field, as would be provided by a miniature multi-leaf collimator, and subsequently use a broader field, as would be provided by a multi-leaf collimator.

SUMMARY OF THE INVENTION

The present invention is directed to a movable, LINAC-mounted miniature multi-leaf collimator which is adapted so that it can be moved into and out of the general radiation field of the LINAC to provide alternate modes of radiation shaping.

In accordance with one preferred embodiment, a LINAC system includes a miniature multi-leaf collimator which is mounted to the radiation head of a LINAC. The miniature multi-leaf collimator includes a mechanism that translates, rotates or otherwise moves the collimator away from the radiation beam path when the system does not need miniature multi-leaf beam shaping. In this way, beams from a multi-leaf collimator, cut block, or jaws can be delivered to the patient without changing the beam orientation of the LINAC and without removing the miniature multi-leaf collimator physically from the head of the LINAC radiation device. The miniature multi-leaf collimator may be connected to a rail or pivot system which enables the collimator to be swivelled or translated out of the region of the radiation beam when it is not used for conformal beam shaping. A multi-leaf collimator, which is also mounted to the LINAC head, can therefore be used to provide larger conformal fields when the miniature multi-leaf collimator is transposed away from the radiation field.

Advantageously, such a "permanently" mounted but movable miniature multi-leaf collimator increases the efficiency of use of the miniature multi-leaf fields and the fields provided by a multi-leaf collimator or other beam-shaping device. Using a single, fixed position of a radiation beam relative to the patient, small conformal fields from the miniature multi-leaf can be delivered, and within seconds the miniature multi-leaf can be translated out of the radiation field, and broader multi-leaf fields can be given to a wider tissue region of the patient. This has the advantage that it improves efficiency and accuracy, allowing concentrated boost fields to tumors to be delivered, and conveniently thereafter, without having to move the beam direction or the patient, delivering broader fields to wider tissue volumes. Advantageously also, the miniature multi-leaf collimator need not be removed from the LINAC, thereby increasing the safety of its use and reducing the chance that the miniature multi-leaf could be accidentally dropped onto the patient or onto the floor, causing injury to the patient or damage to the instrumentation.

BRIEF DESCRIPTION OF THE DRAWINGS

In the drawings, which constitute a part of the specification, exemplary embodiments exhibiting various forms and features hereof are set forth, specifically:

FIG. 6A shows a schematic diagram of one embodiment of a miniature multi-leaf collimator in a radiation field in accordance with the present invention;

FIG. 6B shows the miniature multi-leaf collimator leaves of FIG. 6A pushed back to allow a multi-leaf collimator to define the beam field in accordance with the present invention; and FIG. 7 is a schematic diagram illustrating one embodiment of a movable coupling according to the present invention.

DESCRIPTION OF SEVERAL PREFERRED EMBODIMENTS OF THE INVENTION

Figure 1:
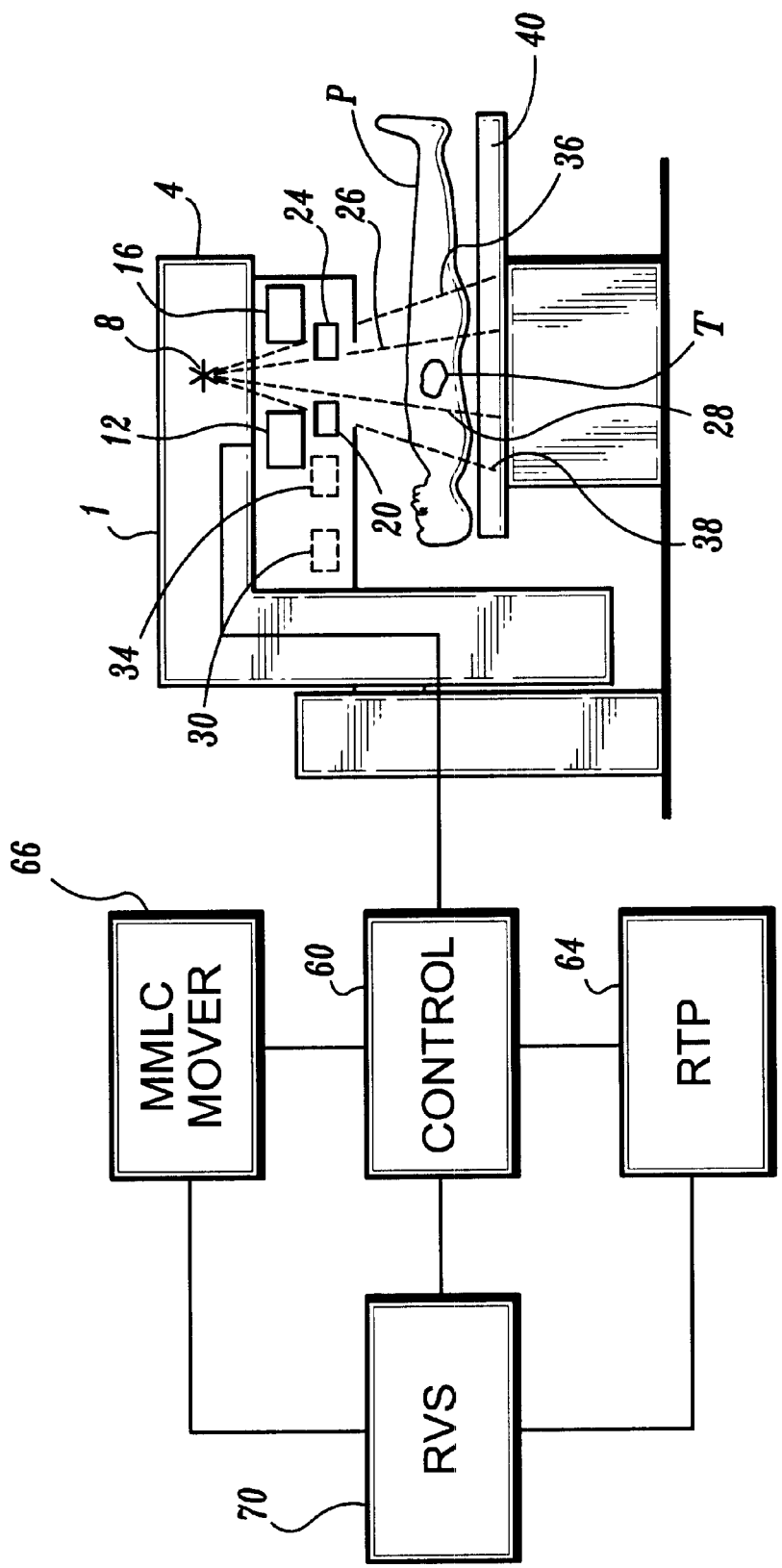
FIG. 1 is a schematic and block diagram of one embodiment of a LINAC and movable miniature multi-leaf collimator in accordance with the present invention.

Referring to FIG. 1, an illustration of one embodiment of a system in accordance with the present invention is shown by a combined block and schematic diagram. A LINAC is represented by element 1. By reference, LINAC configurations with gantries and radiation heads are illustrated by the LINACs of Siemens Oncology Care (Concord, Calif.). A LINAC radiation source of photons, typically X-rays, is represented by element 8.

In the head 4 of the LINAC, a multi-leaf collimator (MLC) or block element is represented by elements 12 and 16. For example, the elements 12 and 16 may be the left bank 12 and right bank 16 of a multi-leaf collimator positioned in the path of the radiation from source 8 to define the contour or shape of the radiation beam profile. Each bank 12 and 16 comprises multiple tungsten leaves that move independently to form a beam shape. Typically such MLC leaves have a width of one centimeter.

Also shown in FIG. 1 is a miniature multi-leaf collimator (MMLC) represented schematically by elements 20 and 24, which may be the left bank 20 and right bank 24 of the multiple leaves of the miniature multi-leaf collimator. Each bank 20 and 24 may include multiple tungsten leaves which move independently to define an MMLC shape. In one embodiment, each of the MMLC leaves may have a width in the range of three to five millimeters. The MMLC leaves may also interrupt the radiation beam from radiation source 8 thereby shaping the beam, as illustrated by dashed lines 26 and 28.

A patient P is illustrated lying on a LINAC couch 40. A target volume T has been defined in the patient's body. The volume T may, for example, be a cancerous tumor which is to be radiated to enable treatment of the cancer by the biological effects of the radiation beam from source 8.

The miniature multi-leaf collimator leaves (banks 20 and 24) provide a contoured delivery of dose by intersecting the radiation from source 8. This shaping of the beam by means of a miniature multi-leaf collimator can provide better contouring delivery to the target volume T while sparing normal tissue around it.

A controller 60 controls the movement of each of the tungsten leaves within each of the leaf banks 20 and 24 and leaf banks 12 and 16, the switching of the source 8 on and off, the control beam dose rates, and the control of the position of the gantry 4. The controller 60 is connected to a record-and-verify system (RVS) 70 which checks and stores parameters of the LINAC and collimator systems. A radiation therapy planning system 64 (RTP) 64, typically delivers a set of beam profiles according to a desired radiation dose plan. These profiles are inputted to the controller 60 to control the position of the LINAC gantry and the multi-leaf or miniature multi-leaf leaf positions according to the desired dose plan.

In accordance with the present invention, also shown in FIG. 1 is a translated or alternate position of the miniature multi-leaf collimator as represented by dashed elements 30 and 34. Elements 30 and 34 may represent, for example, the translated position of the left and rights banks 20 and 26 when they have been displaced away from the main radiation beam. When the miniature multi-leaf collimator is so displaced, the radiation profile from source 8 is then defined by the position of the multi-leaf collimator leaf banks 12 and 16, giving rise to beam edges illustrated by the dashed lines 36 and 38. This is a broader field and will radiate a larger volume of tissue in the patient than the target T.

The movement (e.g. translation) of the miniature multi-leaf between positions is accomplished using a miniature multi-leaf mover, represented schematically by block 66. The mover 60 may comprise a motor system, transporter system, electronic and computer motor controls, a computer controller, sensing devices, and other elements which are associated in the system to translate the miniature multi-leaf collimator as described above and illustrated in FIG. 1. The structure and operation of the mover 66 is described in more detail below.

An advantage of the system in FIG. 1 is that the miniature multi-leaf collimator is not physically removed from the radiation head 4. This has the advantage that when the LINAC 1 is positioned at a fixed orientation to aim radiation from source 8 at a patient P, then this position of the LINAC can remain fixed irrespective of the position of the miniature multi-leaf. For example, in a first position of the miniature multi-leaf collimator, leaf banks 20 and 24 control the beam shape (illustrated by dashed lines 26 and 28). In a second translated position of the MMLC, the miniature multi-leaf leaf banks are translated to positions 30 and 34, and the larger beam profiles (illustrated by lines 36 and 38) are defined by the multi-leaf elements 12 and 16. This aspect of the invention is illustrated in more detail in FIGS. 2A and 2B.

Figure 2A:
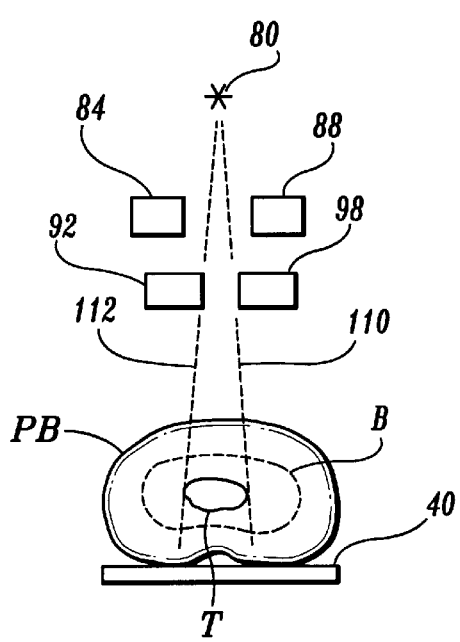
FIG. 2A is a graphical representation of a beam profile from a radiation machine with one embodiment of miniature multi-leaves in position to shape the beam in accordance with the present inventions.

In FIG. 2A the miniature multi-leaf leaves 92 and 98 intercept the radiation from source 80 to provide a beamed profile margin, illustrated by dashed lines 110 and 112. The beam profile conforms to target T according to clinical indications and planning. The patient's body PB is shown in sectional view lying on couch 40 of the LINAC system.

Figure 2B:
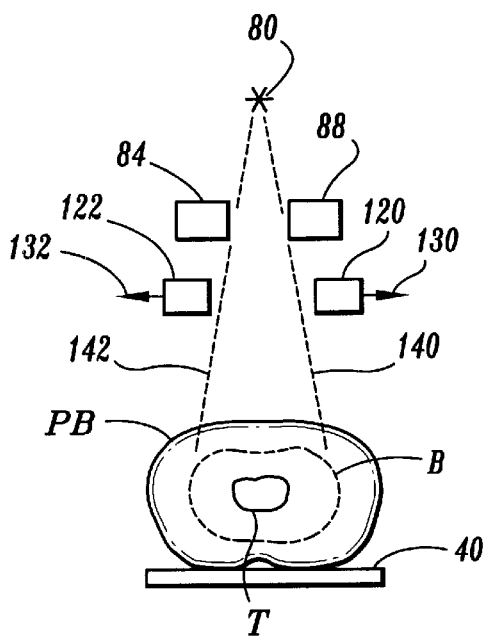
FIG. 2B is a graphic representation of the beam profile of FIG. 2A when the miniature multi-leaves are moved out of the beam in accordance with the present invention.

In FIG. 2B, the left and right banks of opposing multiple miniature multi-leaf leaves, represented by 120 for the right bank and 122 for the left bank, are shown retracted or pulled away from the radiation beam field in the direction of the arrows 130 and 132, respectively. In this translated or moved position of the MMLC, the leaf banks of the multi-leaf collimator (MLC) now define the radiation beam. For example, element 84 may represent the left bank of the MLC, and element 88 may represent the right bank of the MLC. The radiation from source 80 is now defined by the position of the multi-leaf banks 84 and 88, producing the beam profile illustrated by dashed lines 140 and 142. In three dimensions, this will provide dose to a broader region of tissue, illustrated by the dashed line B, which may provide a lower dose and extended boost to involve tissue around the tumor T in the patient's body PB.

Figure 3:
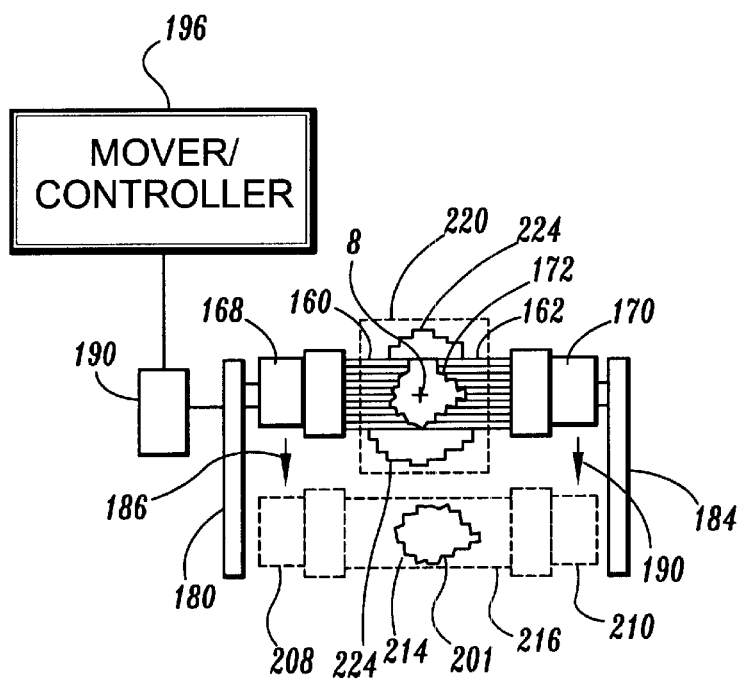
FIG. 3 is a schematic diagram of one embodiment of a movable miniature multi-leaf collimator in accordance with the present invention.

FIG. 3 shows a schematic diagram which views the beam from the direction of the patient. This shows a two-dimensional diagram of planes perpendicular to the beam direction as illustrated, for example, in FIG. 1.

Also shown in FIG. 3 as represented dashed line 220 is the schematic diagram of a multi-leaf collimator which is closer to the source 8 than the miniature multi-leaf collimator and defines a contour shape illustrated by the line 224. By reference, the miniature multi-leaf collimator of Radionics, Inc. defines shaped fields up to 10 centimeters by 12 centimeters in size, and the MLC of Varian, Inc. defines field shapes with widths up to 40 centimeters.

FIG. 3 also shows an embodiment of the present invention that incorporates a translator device for moving the miniature multi-leaf collimator into and out of the radiation field. The left bank of leaves 160 and right bank of leaves 162 of the miniature multi-leaf collimator define a contoured shape 172 to give a conformal, finely-shaped beam delivery to a target. The control of the position and movement of the leaves in banks 160 and 162 can be implemented by banks of individual motors and lead screws driving the leaves, as illustrated by left motor bank 168 and right motor bank 170. The controller for the LINAC, as illustrated in FIG. 1, may comprise a controller system for the leaves and motor positions according to a defined treatment plan. By reference, the MMLC manufactured by Radionics, Inc. (Burlington, Mass.) comprises a system of a miniature multi-leaf collimator, its controller system, and coupling to a treatment planning program. By reference, the multi-leaf collimator of Siemens Oncology Care of Concord, Calif., shows the arrangement, geometry, and profiles typical of a multi-leaf collimator.

In accordance with the invention, the system elements of the miniature multi-leaf collimator can be moved on tracks as illustrated by tracks 180 and 184. Thus, the entire motor system and leaves can be translated, as illustrated by arrows 186 and 190, so that the leaves are moved, for example, to the position illustrated by the dashed lines 214 and 216, and the motors are moved to the position illustrated by the dashed lines 208 and 210. In this position, the contour profile defined by the miniature multi-leaf collimator is illustrated by the line 201. Thus, the contour 201 is displaced sideways from the contour 224 of the multi-leaf collimator 220 and is, therefore, out of the beam field. As a result, after the beam passes through the multi-leaf contour 224, the contour 201 of the mini multi-leaf collimator does not re-define the margin of the beam, as the contour 201 would when it is in the position 172 within the beam.

Translation of the miniature multi-leaf elements, as illustrated in FIG. 3, may be accomplished using, for example, a series of motors, actuators, gear systems, and lead screws, which are represented by block element 190. As an example, the miniature multi-leaf collimator comprising the leaf elements 160 and 162 together with leaf carriers and motor banks 168 and 170 could be analogous to the miniature multi-leaf collimator MMLC manufactured by Radionics, Inc. (Burlington, Mass.). This device assembly could be connected on its ends to ground rods that run (slide) in bushings to implement the travels (tracks) indicated by elements 180 and 184. One direction of movement is illustrated by arrows 186 and 190. A lead screw with motor drives could also be part of the elements 180 and 184.

The movement of the miniature multi-leaf collimator away from and back into the beam field position, as illustrated in FIG. 3, could be controlled by motor controllers, encoders, and stop positions with micro-switches to accurately determine its end points. The controllers for these elements are represented schematically by the block 190 in FIG. 3. The mover electronics, computer control, feedback system, and general controller are illustrated by schematic block 196.

A movable miniature multi-leaf collimator could be translated on the radiation head of the LINAC itself. The entire assembly could rotate together with the LINAC collimator head assembly in a way similar to that of a wedge tray or block accessory tray (devices which are commonly attached to commercial LINACs). The mover/controller 196 may be located at a remote position such as the operator's control station in another room. The mover/controller 196 could have graphics control and menu-driven user interfaces to indicate the position of the miniature multi-leaf.

Figure 4:
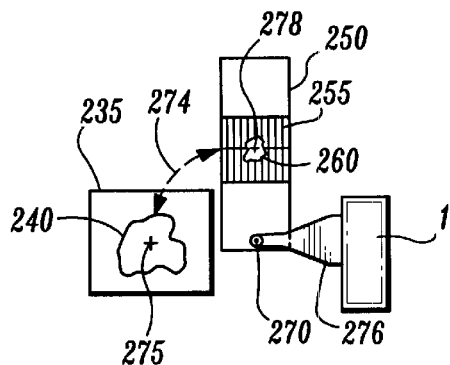
FIG. 4 is a schematic diagram of one embodiment of a movable miniature multi-leaf collimator and a multi-leaf collimator in accordance with the present invention.

FIG. 4 is another embodiment of the present invention that illustrates a rotatable coupling. FIG. 4 is a schematic view looking towards the beam from the view of the patient. This view only includes a schematic representation of the MMLC and other collimator devices. The miniature multi-leaf collimator (MMLC) 250 is an assembly with leaves 255 that move to form an aperture 260. There is a pivot (e.g. an axle and associated bearings) 270 at one end about which the MMLC can rotate, as illustrated by arrow 274. The pivot 270 may be connected to the LINAC 1 via a hinge arm 276. The marking 275 in FIG. 4 illustrates the central axis of the radiation beam projecting through the ideal source of radiation. There is also another conformal collimator structure 235 in place to define a beam shape 240. When the miniature multi-leaf collimator 250 is swung into the position away from the radiation field, as illustrated in FIG. 4, then the beam of radiation is defined by contour 240. However, when the miniature multi-leaf is swung into the position such that its central axis, illustrated by marking 278, is coincident with the central axis of the beam 275, then the radiation beam contour would be defined by the contour line 260 of the miniature multi-leaf collimator 250.

Various arrangements of the MMLC movement are possible to be devised by those skilled in the art. The left and right banks of the miniature multi-leaf may be separable and translated as a unit in opposite directions, as illustrated graphically in FIG. 2. The left and right leaf and motor banks may be pivoted around their own separate axes so as to swing the motor banks and leaves away from the radiation port direction. There may be a gimbal structure or rail track system upon which the miniature multi-leaf collimator can run so as to translate it and move it in a curvilinear direction away from the radiation field so as to tuck in inconspicuously to the gantry of the LINAC 1 (FIG. 1). The movement of MMLC away from the radiation field may be accomplished using electromechanical and automatic devices or may be performed manually by the operator. The sequencing of the movement of the miniature multi-leaf collimator can be integrated with the sequencing of the motion of the leaves of the miniature multi-leaf collimator according to the clinical prescription of radiation. The miniature multi-leaf collimator may be translated on the radiation head of the LINAC so as to accommodate different port positions, for example LINAC gantry, couch, and collimator angles, and different degrees of movement to or away from the radiation field according to clinical usage.

In another embodiment of the present invention, the movable miniature multi-leaf collimator MMLC may be substituted by various forms of other collimation systems including standard multi-leaf collimators with broader leaves, multi-leaf collimators with leaves of varying thickness, variable block and jaw collimator systems, and other collimator systems devised by those skilled in the art.

Figure 5:
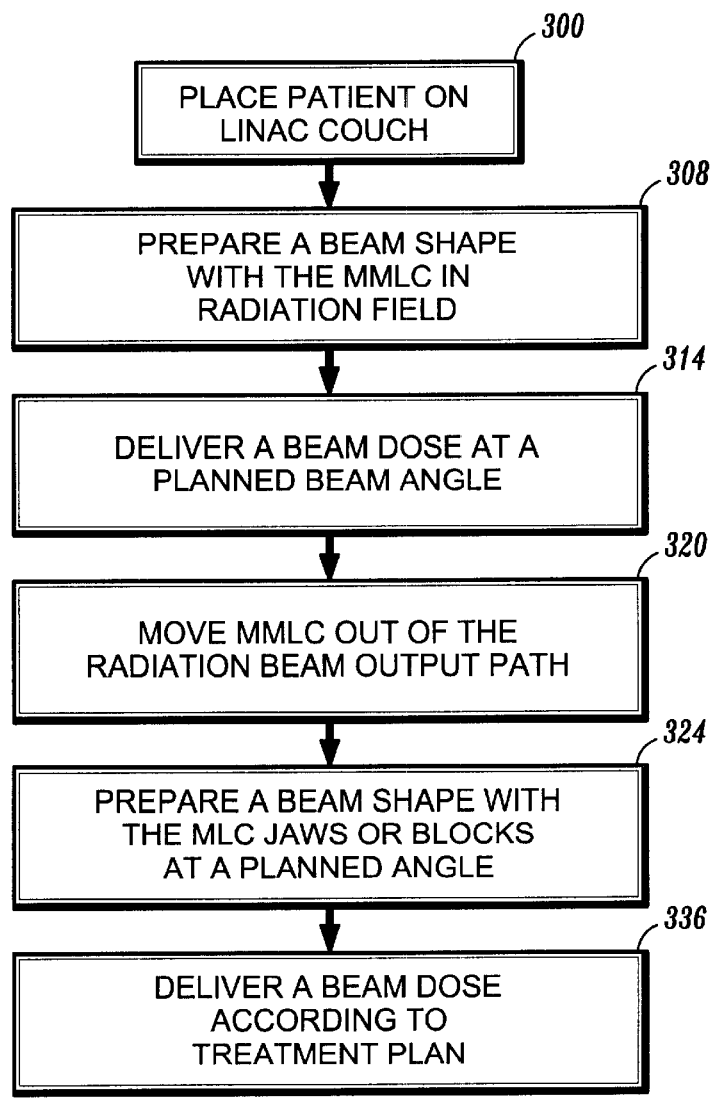
FIG. 5 shows a process of using a movable miniature multi-leaf collimator in accordance with the present invention.

FIG. 5 illustrates one embodiment of operation of the system and method in accordance with the present invention as shown with a flow diagram. As a preliminary step, a treatment plan may be developed based on image scan data. By reference, the stereotactic treatment planning system product XKnife manufactured by Radionics, Inc. (Burlington, Mass.) illustrates the use of treatment planning based on various imaging modalities to define target volumes and beam positions and shapes. As represented by block 300, a patient is placed on the radiation delivery machine couch (in this case a LINAC). According to the prescribed treatment plan, the miniature multi-leaf collimator attached to the LINAC is moved into the beam field position and the shape of the miniature multi-leaf collimator beam contour is prepared by the controller system of the LINAC and miniature multi-leaf collimator (block 308). When confirmation has been made that the beam shape of the MMLC is correct, for example by a record-and-verify system, and the LINAC gantry couch and gantry angles are set according to plan, the radiation beam is delivered from the radiation source through the collimator aperture of the miniature multi-leaf collimator to the desired location in the patient's body (block 314). Once the beam radiation is completed for that sequence, the miniature multi-leaf collimator is moved out of the radiation beam path (block 320). This may be done automatically or by operator control. In the next step according to the treatment planning, a second collimator device such as a multi-leaf collimator, a set of collimation jaws, or another radiation block system in the beam path is prepared to define the appropriate beam shape at the proper LINAC and couch angle according to the treatment plans (block 324). The beam is then activated and a dose of radiation is delivered to the patient through the beam aperture port, as defined in block 324, and the radiation dose is terminated when the appropriate clinical effect has been achieved according to the treatment plan (block 336). This sequence of steps illustrates a process by which radiation can be delivered to a patient with both a miniature multi-leaf collimator that can be moved in and out of the radiation field and another secondary radiation collimation device which is also in place within the radiation field at the time when the miniature multi-leaf collimator has been moved out of the radiation field. Thus, different configurations of beam shapes can be achieved within short time sequences of each other to deliver varied radiation patterns according to clinical needs and in accordance with the present invention.

Variations of the process and configurations of the above figures are possible by those skilled in the art. Variations in the form, configuration, and application of the miniature multi-leaf collimator are possible. The miniature multi-leaf collimator may be substituted with a multi-leaf collimator or standard leaf width that can be moved in and out of the radiation field. Various control devices and quality assurance devices can be put into place. Variations of the means and geometry by which the miniature multi-leaf can be translated in and out of the radiation field can be devised. One or more collimators may be adapted to be moved into or out of the beam field.

FIG. 6A and FIG. 6B illustrate another embodiment in accordance with the present invention showing schematically how the miniature multi-leaf collimator can be moved away from the radiation field. These diagrams are schematic diagrams looking from, for example, the position of the patient target towards the beam source in the LINAC. FIGS. 6A and 6B describe a translation or displacement movement of the left bank of leaves and the right bank of leaves, as illustrated by elements 92 and 98 in FIG. 2A. Referring to FIG. 6A, a left bank of leaves 400 opposes a right bank of leaves 406 comprising the shape-defining elements of the MMLC miniature multi-leaf collimator. They are carried in leaf carriers, illustrated by left leaf carrier 420 and right leaf carrier 424. Further, motor and encoder banks are illustrated by a left motor bank 430 and a right motor bank 434. Together, for example, the elements 400, 420, and 430 may be described as constituting the left leaf bank of a miniature multi-leaf collimator, and the elements 406, 424, and 434 may be described to comprise the right leaf bank of a miniature multi-leaf collimator. The individual leaves of the leaf banks 400 and 406 move in opposing, parallel directions and, when appropriately positioned, define a beam aperture 410.

Referring to FIG. 6B, the left and right leaf banks of the miniature multi-leaf collimator are displaced in position, as illustrated by the arrow 450 for the displacement of the left leaf bank and the arrow 456 for displacement of the right leaf bank. By movements away from the central beam position, illustrated by the mathematical cross point 550 in FIGS. 6A and 6B, the leaves 440 and 446 of the miniature multi-leaf collimator are retracted away from the beam field from the LINAC. In the position of FIG. 6B, the radiation field may now be defined by a second collimator device such as a multi-leaf collimator, beam block, set of jaws, and so on. For example, the elements 500 may represent the left bank of leaves of a multi-leaf collimator, and the elements 506 may illustrate the right bank of leaves of a multi-leaf collimator. These leaves would be part of a multi-leaf collimator, as for example illustrated in FIG. 2A by the left and right elements 84 and 88, as described above. With the miniature multi-leaf leaves in position 440 and 446, as shown in FIG. 6B, the aperture of the multi-leaf collimator, illustrated by contour 510, now defines the beam shape. Various methods of moving, translating, or displacing the left and right bank of the miniature multi-leaf collimator can be devised by those skilled in the art. For example, these methods may incorporate systems of rails, slide rods, linear translation devices, geared rack and pinion assemblies.

As illustrated in FIG. 7, the mover 60 of FIG. 1 may include a movable coupling 42 that is attached to the LINAC 1 and to the miniature multi-leaf collimator (MMLC) 44.

The coupling 42 is movable in that it enables the MMLC 44 to move relative to the LINAC 1, for example, as represented by arrow 46. A variety of coupling structures may be used in accordance with the invention.

The primary function of the coupler 42 is to accurately position the MMLC 44 when the MMLC 44 is in the beam path and, as necessary, to move the MMLC 44 to an alternate position (e.g., as represented in phantom by block 48). Thus, the MMLC 44 may be moved out of the beam path of interest so that the beam will be shaped by the MLC 45. For example, in FIG. 7 the coupling 42 includes a drive shaft 50 for moving the MMLC 44 in the directions represented by arrow 46. The drive shaft 50 connects to a drive unit 52 and the MMLC 44 via couplers 51 and 52. Alternatively, the drive unit 52 may connect to a screw drive, a pneumatic piston, a belt or pulley assembly, or a gear drive assembly to move the MMLC 44. Typically, the drive unit 52 operates under the control of a controller 56.

A position sensor 54 may be used to determine the position of the MMLC 44 relative to the LINAC 1. In one embodiment position signals from the sensor 54 are sent to the controller 56. The controller 56, in turn, controls the drive unit 56 to position the MMLC 44 at the desired location.

Various processes and methods of use of a movable miniature multi-leaf collimator can be devised by clinicians and those skilled in the art. For example, variations or perturbations of the sequence illustrated in FIG. 5 for the use of the movable miniature multi-leaf collimator in conjugation with other collimator systems and with other radiation delivery systems other than LINACs may be devised. The LINAC may be replaced by a robotic LINAC or another type of ionizing radiation machine.

In view of these considerations, as will be appreciated by persons skilled in the art, implementations and systems could be considered broadly and with reference to the claims set forth below.

What is claimed is:

1. A linear accelerator system for applying radiation treatment, which comprises:
    a linear accelerator adapted to provide an output beam of radiation having a radiation out field;
    a first multi-leaf collimator connected to the linear accelerator and having multiple leaves being relatively movable to define a first variable radiation beam field from radiation emitted from the linear accelerator; and
    a second multi-leaf collimator connected to the linear accelerator and having multiple leaves being relatively movable independent of the first moving multi-leaf collimator to define a second variable radiation beam field from radiation emitted from the linear accelerator
    wherein a first predetermined size beam dosage of radiation may be delivered to a target treatment site by the linear actuator as defined by the first multi-leaf collimator and thereafter the first multi-leaf collimator is retracted and a second predetermined size beam dosage of radiation, different from the first predetermined size beam, may be delivered to the target treatment site as defined by the second multi-leaf collimator.

2. A linear accelerator system as recited in claim 1, wherein the first multi-leaf collimator includes at least two banks of leaves movable relative to each other to define an aperture.

3. A linear accelerator system as recited in claim 2, wherein the second multi-leaf collimator includes at least two banks of leaves movable relative to each other to define an aperture.

4. A linear accelerator system as recited in claim 2, wherein each leaf of the first multi-leaf collimator has a width less than each leaf of the second multi-leaf collimator.

5. A linear accelerator system for applying radiation treatment, which comprises:
    a linear accelerator adapted to provide an output beam of radiation having a radiation out field;
    a first multi-leaf collimator connected to the linear accelerator and having multiple leaves being relatively movable to define a first variable radiation beam field from radiation emitted from the linear accelerator;
    a first controller operatively connected to the first multi-leaf collimator to selectively configure an aperture of the first multi-leaf collimator;
    a second multi-leaf collimator connected to the linear accelerator and having multiple leaves being relatively movable independent of the first moving multi-leaf collimator to define a second variable radiation beam field from radiation emitted from the linear accelerator;
    a second controller operatively connected to the second multi-leaf collimator to selectively configure an aperture of the second multi-leaf collimator;
    wherein during a single treatment session, a first predetermined size beam dosage of radiation may be delivered to a target treatment site by the linear actuator as defined by the first multi-leaf collimator and thereafter the first multi-leaf collimator is retracted and a second predetermined size beam dosage of radiation, different from the first predetermined size beam, may be delivered to the target treatment site as defined by the second multi-leaf collimator.

6. A linear accelerator system as recited in claim 5, wherein the first multi-leaf collimator includes at least two banks of leaves movable relative to each other to define an aperture.

7. A linear accelerator system as recited in claim 6, wherein the second multi-leaf collimator includes at least two banks of leaves movable relative to each other to define an aperture.

8. A linear accelerator system as recited in claim 6, wherein each leaf of the first multi-leaf collimator has a width less than each leaf of the second multi-leaf collimator.

9. A method of applying different shaped radiation beams to a patient during a single treatment session with a linear accelerator comprising the steps of:
    defining a first radiation beam field by adjusting an aperture of a first movable multi-leaf collimator connected to a linear accelerator in between a radiation source of the linear accelerator and a patient;
    delivering a first radiation treatment to a target site of a patient in the first radiation beam field;
    defining a second radiation beam field, differing in size from the first radiation beam field, by adjusting an aperture of a second movable multi-leaf collimator connected to the linear actuator, and independently controlled from the first movable multi-leaf collimator in between the radiation source and the patient; and
    delivering a second radiation beam field to the target site of the patient in the second radiation beam field during the same treatment session as the first radiation beam field.

* * * * *